United States Patent [19]

Brantl

[11] Patent Number: 4,657,892

[45] Date of Patent: Apr. 14, 1987

[54] PHARMACOLOGICALLY ACTIVE PEPTIDES

[76] Inventor: Victor Brantl, Frauenplatz 10, D-8000 München 2, Fed. Rep. of Germany

[21] Appl. No.: 740,066

[22] PCT Filed: Sep. 13, 1984

[86] PCT No.: PCT/DE84/00191
  § 371 Date: May 13, 1985
  § 102(e) Date: May 13, 1985

[87] PCT Pub. No.: WO85/01292
  PCT Pub. Date: Mar. 28, 1985

[30] Foreign Application Priority Data

Sep. 19, 1983 [DE] Fed. Rep. of Germany ....... 3333752

[51] Int. Cl.$^4$ ..................... A61K 37/24; C07K 7/06; C07K 7/44
[52] U.S. Cl. ........................ 514/16; 514/17; 514/809; 530/302; 530/329; 530/330
[58] Field of Search ............. 260/112.5 E, 112.5 R; 514/16, 17, 809; 530/302, 329, 330

[56] References Cited

U.S. PATENT DOCUMENTS 4,254,024  3/1981  Stewart et al. ............ 260/112.5 R

*Primary Examiner*—Delbert R. Phillips
*Attorney, Agent, or Firm*—Marshall, O'Toole, Gerstein, Murray & Bicknell

[57] ABSTRACT

Pharmacologically active peptides of the following formulas are described:

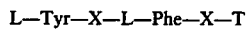

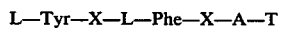

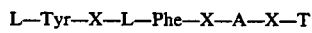

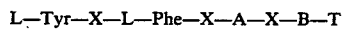

in which L—Tyr is the N-terminal amino acid residue L-tyrosine, X any amino acid residue of the D-form, L—Phe is the amino acid L-phenylalanine, A and B are any desired amino acid residues and T is the C-terminal carboxyl group, which is further disclosed in the description.

The substances are suitable for the therapy of diseases.

6 Claims, No Drawings

PHARMACOLOGICALLY ACTIVE PEPTIDES

DESCRIPTION

In the German application DT-OS No. 29 36 099, which crresponds to U.S. Pat. No. 4,390,527, pharmacologically active peptides are described, in particular peptides with opiate-like activity, which are more potent in opiate-like activity and which have a higher stability against proteolytic enzymes (for example contained in rat plasma) when compared to the peptides described in DT-OS No. 29 21 216, corresponding to U.S. patent application Ser. No. 229,577 filed Jan. 22, 1981. The peptides of the DT-OS No. 29 36 099 have the following basic structure:

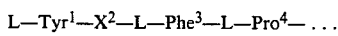

L—Tyr[1]—X[2]—L—Phe[3]—L—Pro[4]— ...

in which L—Tyr is equal to L-tyrosine, X is equal to any amino acid in the D-form, L—Phe is equal to L-phenylalanine and L—Pro is equal to L-proline. It should already be mentioned now that according to the DT-OS No. 29 36 099 the amino acid in position 4 is in the L-form; the D-form is not mentioned. It has been demonstrated, that these peptides have only a determined maximal potency, especially opiate-like (see table 1, page 13).

In the German application DT-OS No. 30 34 897, which is very similar to the DT-OS No. 29 36 099 pharmacologically active peptides of the following basic structure are described:

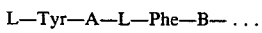

L—Tyr—A—L—Phe—B— ...

in which L—Tyr is equal to L-tyrosine, A is a D-amino acid, L—Phe is equal to phenylalanine and B is a neutral L-amino acid residue (i.e. glycine). Also here it should be mentioned that the amino 4th acid residue should be of the L-form.

In addition, it should be mentioned that the peptides of the European application No. 81305519.1 (publication No. 0053029) are essentially identical with those of the already mentioned DT-OS No. 29 21 216. The European application No. 81305519.1 has, however in the position of the 4th amino acid residue in the peptide a D-amino acid, but it was not realised, that a particular potent opiate-like effect resulted through a combination of a D—Ala residue in the second position together with a D-Proline residue in the position 4. Additionally the peptides of the Europ. application No. 8130519.1 have the disadvantage, that they are rapidly degraded in the blood and that they show by this only shortly lasting pharmacological effects in the living organism. (This degradation is prevented by introduction of a D-alanine residue in position 2). Detailed data on this are described in the DT-OS No. 29 21 216 and DT-OS No. 29 36 099.

It is an object of this invention to provide new pharmacologically active peptides, in particular opiate-like, which exhibit more potent pharmacological effects, in particular opiate-like and/or which exhibit a higher stability against proteolytic enzymes.

These objects are satisfied according to the invention in that the pharmacologically active peptides have the following formula:

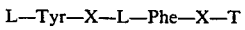

L—Tyr—X—L—Phe—X—T

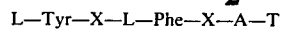

L—Tyr—X—L—Phe—X—A—T

L—Tyr—X—L—Phe—X—A—X—T

L—Tyr—X—L—Phe—X—A—X—B—T wherein L—Tyr is the N-terminal amino acid residue L-tyrosine, X is any amino acid of the D-form, L—Phe is the amino acid residue L-phenylalanine. A and B may represent any amino acid residue. T represents OH, OR, $NH_2$, NHR, $NR_2$ or NH NHR', at which R has, if necessary, the following meaning: a substituted linear or branched $C_{1-10}$-alkyl, adamantyl, $C_{1-10}$-cycloalkyl or $C_{6-8}$-aralkyl, suitable phenyl, benzyl or means phenylethyl and R' hydrogen, linear or branched $C_{1-10}$-alkyl, cycloalkyl or $C_{6-8}$-aralkyl, $C_{2-8}$-alkenyl, linear, branched or cyclic aliphatic $C_{1-16}$-acyl, if appropriate substituted by OH, $NH_2$, $C_{1-4}$-alkoxy or halogen, aromatic acyl, if appropriate substituted by OH, $NH_2$, halogen, or $C_{1-4}$-alkoxy; linear, branched or cyclic $C_{3-11}$-aliphatic urethan or aromatic urethan and their pharmaceutically acceptable salts.

According to the invention, the peptides have in contrast to that described in the prior art a higher opiate-like activity and/or an increased stability against proteolytic enzymes (see example).

According to a further development of the invention the peptides are characterized in that the amino acid residue X is replaced by the following amino acids:

D-alanine, D-threonine, D-serine, D-methionine, D-valine, D-phenylalanine, D-leucine, D-isoleucine, D-arginine, D-histamine, D-proline, D-hydroxyproline, D-lysine, D-glutamine, D-glutamic acid, D-asparagine, D-aspartic acid and A, B are replaced by the aromatic amino acids tyrosine and phenylalanine or glycine.

The particular properties of the peptides according to the invention are probably totally or partially attributable to the special position of the D-amino acid residues. They are in particular those on position 2 (calculated from the tyrosine) and position 4, which mediate the high enzymatic stability and the high opiate-like effect (see example).

According to another further development the peptides are characterized in that the N-terminal tyrosine is of the following formula:

(a)

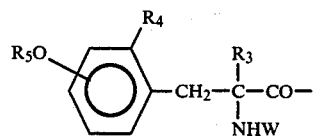

wherein means $R_3$ for hydrogen or an alkyl group with 1 to 4 C-atoms $R_4$ for hydrogen or together with $R_3$ for an ethylene bond $R_5$ for hydrogen, an alkyl group with 1 to 4 C-atoms or a $R_6$CO-group $R_6$ for a saturated or unsaturated linear or branched alkyl residue with 1 to 17 C-atoms, a phenyl residue or a phenyl-alkyl alkyl residue with 7 to 12 C-atoms, wherein the phenyl residues can be substituted by 1 or 2 substituents from the halogen series, alkyl with 1 to 4 C-atoms or alkoxy with 1 to 4 C-atoms, wherein the $R_5O$-group is in the meta position or para position to

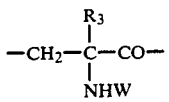

W for hydrogen, alkyl with 1 to 5 C-atoms, alkenyl with 3 to 5 C-atoms, cyclopropylmethyl, cyclobutylmethyl, $R_6CO-$.

(b) the phenylalanine of the general formula:

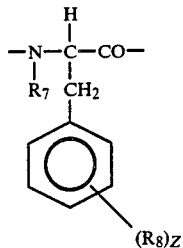

is substituted by:
- $R_7$ for hydrogen of alkyl with 1 to 4 C-atoms
- $R_8$ for hydrogen, fluorine, chlorine, bromine, nitro, alkyl with 1 to 4 C-atoms or alkoxy with 1 to 4 C-atoms
- Z for 1 or 2 substituents.

This development has the advantage, that by introduction of halogens such as Cl or F in the aromatic ring of the phenylalanine, the lipophilicity of the substances will be increased in such manner that they penetrate easier from blood into the central nervous system and by this less substance will be needed for the same effects. The same effect has an introduction of a N-methyl-group in the phenylalanine residue.

The peptides according to the invention may be characterized in that the amino acid residues alanine, phenylalanine as well as A and B are dehydro amino acids.

For a further increase of the enzymatic stability the phenylalanine in position 3 of the peptide can be of the D-form. Surprisingly this does not cause any loss of opiate-effects and leads to a still higher enzymatic stability of the peptides.

The peptides according to the invention exhibit strong effects upon the central nervous system. This can be in particular strong opiate-like (analgetic) effects as well as cataleptic effects. In addition effects may be observed, which have to be determined as neuroleptic-like.

The peptides according to the invention exhibit effects upon the cardiovascular system. This can be in particular a blood pressure lowering effect.

The peptides according to the invention can be applied in different forms (for example tablets or in solution); the way of application can be oral, parenteral (i.e.: i.v., i.m., s.c.), transdermal, nasal, vaginal or rectal. In the different galenic formulations can be contained formulating adjuvants which increase the absorption.

The doses of active components in a pharmaceutical preparation can be very different due to the various routes of application. Generally a dose range from 0.001 to 100 mg of active substance per kilogram body weight can be considered which has to be applied to the mammalian organism to obtain a therapeutic effect such as for example analgesia.

According to further favorable development of the invention the peptides are characterized by the following structures:

Tyr—D—Ala—Phe—D—Ala—Tyr—NH$_2$

Tyr—D—Ala—Phe—D—Ala—Phe—NH$_2$

Tyr—D—Ala—Phe—D—Ala—Tyr—D—Pro—NH$_2$

Tyr—D—Ala—Phe—D—Ala—Phe—D—Pro—NH$_2$

Tyr—D—Ala—Phe—D—Ala—Tyr—D—Pro—Ser—NH$_2$

Tyr—D—Ala—Phe—D—Ala—Phe—D—Pro—Ser—NH$_2$

Tyr—D—Ala—Phe—D—Ala—Tyr—D—Ala—Ser—NH$_2$

Tyr—D—Ala—Phe—D—Ala—Phe—D—Ala—Ser—NH$_2$

Tyr—D—Ser—Phe—D—Ala—Tyr—NH$_2$

Tyr—D—Ser—Phe—D—Ala—Phe—NH$_2$

EXAMPLE

Initially the synthesis of two peptides according to the invention will be described, later on the pharmacological properties of these peptides will be discussed.

SYNTHESIS OF TWO PEPTIDES ACCORDING TO THE INVENTION

The synthesis of the two peptides Tyr—D—Ala—Phe—D—Ala—Tyr—NH$_2$, Tyr—D—Ala—Phe—D—Ala—Phe—NH$_2$ was performed as described by Lottspeich et al. (Hoppe Seyler's Z. Physiol. Chem., 361, 1835-1839 (1980) and in the German application DT-OS No. 29 36 099). The synthesis steps should be shortly mentioned.

The different amino acid residues and the dipeptide, resp., have been purchased from Bachem AG, Bubendorf, Switzerland or from Fluka, Buchs, Switzerland.

STEP 1

(a)

Preparation of the mixed anhydride Z—D—Ala 335 mg Z—D—Ala (1.5 mmol), Z is the protective group benzyloxycarbonyl, are dissolved in 15 ml dimethylformamide (DMF) by adding 170 μl (1.5 mmol) of N-methylmorpholine and reacted with 180 μl (1.4 mmol) chlorine-formic acid-isobutyl ester at −15° C. for 15 minutes.

(b)

Preparation of the amino component 195 mg (1.0 mmol) tyrosine methyl ester (or 178 mg phenylalanine methyl ester) are dissolved in 20 ml DMF by adding 110 μl (1.0 mmol) N-methylmorpholine at −15° C.

After preparation, the amino component is added to 1 (a) and the solution kept for 12 hours at the above mentioned temperature.

Before the further procedures, the surplus of mixed anhydride is destroyed: At 0° C. the pH of the reaction product is set at 8 with an aqueous, saturated KHCO₃—solution and stirred for 30 min at 0° C.

Thereafter, the dipeptide was extracted with ethyl acetate (Etac); the Etac/peptide mixture was washed five times with 20 ml of a saturated sodium chloride/water solution. After two additional washing steps with 10 ml water the Etac-phase was evaporated.

The removal of the protecting group is performed by hydrogenation; the dipeptide was dissolved in 30 ml methanol and 100 mg of palladium-carbon catalyst (Merck, Darmstadt) added. After replacement of the air in the reaction vesel by nitrogen, hydrogen was introduced. The hydrogenation is carried out at 25°-30° C. When no more precipitation occurs in baryta water, the hydrogenation will be stopped. The solution was filtered, washed with water and the filtrate was evaporated on a rotary evaporator. The remaining intermediate product is then used as the amino component in the next step.

STEP 2

(a)

Preparation of the mixed anhydrid Z—D—Ala—Phe 600 mg (1.6 mmol) Z—D—Ala—Phe are prepared as described in Step 1(a).

(b)

The dipeptide D—Ala—Tyr—OMet which was prepared in Step 1 or the D—Ala—Phe—OMet, which was prepared analogously, is dissolved as described in Step 1(b) and mixed together with the mixed anhydride of Step 2(a), 12 hours at −15° C.

The further procedures such as extraction and hydrogenation was performed as described in Step 1.

As final products of Step 2 D—Ala—Phe—D—Ala—Tyr—OMet or D—Ala—Phe—D—Ala—Phe—OMet are obtained.

STEP 3

(a)

Preparation of the mixed anhydride of Z—Tyr 629 mg (1.4 mmol) Z—Tyr, 160 μl (1.4 mmol) N-methylmorpholine and 170 μl (1.3 mmol) of chlorineformic acid-isobutyl ester are dissolved in 15 ml DMF as previously described.

(b)

Preparation of the amino component

The tetrapeptides of Step 2 (see above) are each dissolved in 15 ml DMF and mixed with the mixed anhydride from Step 3(a). The further procedures are carried out as already described.

STEP 4

After removal of the protecting group the peptide methyl esters are submitted in an usual manner to an ammonolysis to form the corresponding amides.

STEP 5

After the ammonolysis the peptides are purified as described in Hoppe Seyler's Z. Physiol. Chem., 361, p. 1836 (1980). The synthesis endproduct is purified by gel-filtration and analized for amino acid content.

The amino acid analysis corresponded to the structure of the invented peptides.

The following part deals with the pharmacological properties of the peptides according to the invention.

In the same way as previously described according to the invention, the other peptides can be prepared, such as for example,

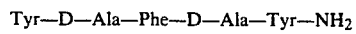
Tyr—D—Ala—Phe—D—Ala—Tyr—NH₂

Tyr—D—Ala—Phe—D—Ala—Phe—NH₂

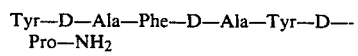
Tyr—D—Ala—Phe—D—Ala—Tyr—D—Pro—NH₂

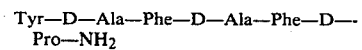
Tyr—D—Ala—Phe—D—Ala—Phe—D—Pro—NH₂

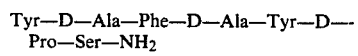
Tyr—D—Ala—Phe—D—Ala—Tyr—D—Pro—Ser—NH₂

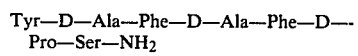
Tyr—D—Ala—Phe—D—Ala—Phe—D—Pro—Ser—NH₂

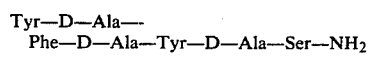
Tyr—D—Ala—Phe—D—Ala—Tyr—D—Ala—Ser—NH₂

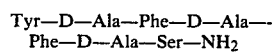
Tyr—D—Ala—Phe—D—Ala—Phe—D—Ala—Ser—NH₂

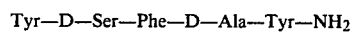
Tyr—D—Ser—Phe—D—Ala—Tyr—NH₂

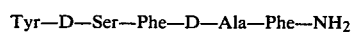
Tyr—D—Ser—Phe—D—Ala—Phe—NH₂

These peptides are in part more potent opiate-like compounds and/or have a higher stability against proteolytic enzymes when compared to the peptides III and IV described in table 1 (see below).

BIOLOGICAL ACTIVITIES OF TWO PEPTIDES ACCORDING TO THE INVENTION

In table 1 the pharmacological properties of two peptides according to the invention are presented and compared to peptides described in the literatur.

As biological test system for determination of the opioid activity the ileum preparation of the guinea-pig was used (detailed description German application No. 29 21 216, p. 24). By this test those substance concentration (nM) have been determined which inhibit the electrically induced contractions of this organ preparation by 50% (so called IC₅₀-values). In addition for a better understanding the IC₅₀-value can be expressed as 100% for the opiates normorphine and dermorphin (DT-OS No. 30 34 897) and the relative activity of the single substances can be given in comparison to normorphine or dermorphine. The indication of the relative potency has the advantage that by this variations of the sensitivity of the assay are neutralized.

The (*) marked values of table 1 correspond to those which have been described by Castiglione et al. (Peptides, 2, p. 266, table 1, substances 1 and 3: column GPI=guinea-pig ileum preparation).

TABLE 1

| No | Substance | IC$_{50}$ | rel. value Nor. = 100 | rel. value Der. = 100 |
|---|---|---|---|---|
| — | Normorphine | 110 | 100 | 3.2 |
| — | Dermorphin | 3.5* | 3143 | 100 |
| I | Tyr—D-Ala—Phe—Pro—Tyr—NH$_2$ | 100 | 110 | 3.5 |
| II | Tyr—D-Ala—Phe—Gly—Tyr—NH$_2$ | 7* | 1571 | 50 |
| III | Tyr—D-Ala—Phe—D-Ala—Tyr—NH$_2$ | 14 | 786 | 25 |
| IV | Tyr—D-Ala—Phe—D-Ala—Phe—NH$_2$ | 2.5 | 3667 | 140 |

IC$_{50}$-values (nM), see description, of two peptides of the invention (III an IV) in comparison to those of the prior art (dermorphin,I,II) as measured in the isolated guinea-pig ileum. The IC$_{50}$-values have been determined from 7 different experiments, the standard deviation of a single value from mean value is less than ±14%. The inhibiting effect of the substances I, II, III, and IV was antagonized by addition of the specific opiate antagonist naloxone (final concentration in the organ bath 900 nM); upon further addition of the substances I to IV to the organ bath (in presence of naloxone) no further inhibition could be observed; the inhibiting effect of the substances I-IV has therefore to be considered as specific opiate-like.

Tab. 1 shows, that the invented peptides III and IV have a remarkable higher opiate-like activity when compared to peptide I of the prior art (DT-OS No. 29 36 099), i.e. have lower IC$_{50}$-values. The peptide IV according to the invention has also a higher opiate-like activity when compared to peptide II of the prior art (DT-OS No. 30 34 897); however, the peptide III has not a higher activity when compared to peptide II of the prior art, but has a higher stability towards proteolytic enzymes (compared to II) and is therefore more suitable for a in vivo application to obtain pharmacological effects.

The peptides according to the invention exhibit not only in vitro but also in vivo strong opiate-like effects (analgesia). The test system employed was the electrically stimulated rat tail. The method was used as described by Brantl et al., 1981, Life Sciences, 28, 1903-1909. The substances have been applicated intraventricularly.

The in vivo relative potency (analgesia) of the substances described in table 1 (together with dermophin as reference compound) corresponded approximately to the relative potency determined by use of the isolated guinea-pig ileum assay.

ENZYMATIC STABILITY OF THE PEPTIDES ACCORDING TO THE INVENTION 1 mg of each of the peptides dermorphin, I, II, III and IV (table 1) were dissolved in 1 ml freshly prepared Krebs-Ringer solution and mixed together with 50 μg α-chymotrypsin (Serva, Heidelberg, dissolved in 50 μl Krebs-Ringer solution); immediately after mixing, a 100 μl aliquot was removed and heated up to 95° C. for 15 minutes. (The heating was employed in order to inactivate the enzyme). This aliquot removed, will be later used for reference as initial value (Zero-value of incubation time). The remaining 950 μl of the peptide/enzyme mixture were incubated for 5 hours at 37° C.; the incubation period was also terminated by heating up to 95° C.

After centrifugation identical aliquots of the supernatants were assayed quantitatively for their opiate-like effect and compared with the zero-value; and guinea-pig ileum was also used as assay system (as above described). It could be demonstrated that, after the 5 hours incubation period, the opiate-like activity in the incubation batch with dermorphin and the peptide II was nearly fully destroyed when compared to the zero-value, the peptides III and IV however, exhibited still their full opiate-like activity, i.e. the inhibition of guinea-pig ileum preparation which was observed upon addition of an aliquot of the zero-value corresponded to the inhibition induced by the same aliquot volume of the 5 hours incubation batch. The substance I shows a higher stability than substance II, but is however, remarkably less active in opiate-like activity when compared to the invented peptides III and IV.

In summary it can concluded that the introduction of a D-amino acid in position 4 of the known peptides I and II is particularly relevant for obtaining an especially high opiate-like activity and/or to obtain peptides which exhibit a particularly high stability against proteolytic enzymes. It is well-known that peptides which usually are employed to obtain pharmacological effects, are quickly metabolized by proteolytic enzymes; this metabolism largly restrict their use as pharmaceuticals.

EXAMPLE FOR A PHARMACEUTICAL PREPARATION (TABLET)

Substance III (table 1): 140 mg
Lactose: 480 mg
Corn starch: 20 mg
Polyvinylpyrrolidon (PVP): 10 mg
Magnesium stearate: 10 mg The substance is mixed together with lactose and corn starch and granulated with a solution of PVP (50% in aqueous ethanol). The granulate will be dried; after addition of magnesium stearate the mixture is compressed to form a tablet.

We claim:

1. Pharmacologically active peptides of the following formulas:

L—Tyr—X—L—Phe—X—A—T

L—Tyr—X—L—Phe—X—A—X—T

L—Tyr—X—L—Phe—X—A—X—B—T wherein:
L—Tyr is the N-terminal amino acid residue L-tyrosine;
X is any amino acid of the group consisting of D-alanine, D-threonine, D-serine, D-methionine, D-valine, D-phenylalanine, D-leucine, D-isoleucine, D-arginine, D-histamine, D-proline, D-hydroxyproline, D-lysine, D-glutamine, D-glutamic acid, D-asparagine and D-aspartic acid;
L—Phe is the amino acid residue of L-phenylalanine;
A represents an aromatic amino acid selected from the group consisting of tyrosine and phenylalanine;
B represents tyrosine, phenylalanine or glycine;

T represents OH, OR, NH$_2$, NHR, NR$_2$ OR
NH—NHR' in which R is a substituted linear or
branched 1-10C-alkyl, adamantyl, 1-10C-cycloalkyl or 6-8C aralkyl, phenyl, benzyl or phenylethyl
and R' represents hydrogen, linear or branched
1-10C alkyl, cycloalkyl or 6-8C-aralkyl, 2-8C-alkenyl, linear, branched or cyclic aliphatic 1-16C-acyl, which can be substituted by OH, NH$_2$, 1-4C-alkoxy or halogen, aromatic acyl which can be
substituted by OH, NH$_2$, halogen, or 1-4C-alkoxy;
linear, branched or cyclic 3-11C-aliphatic urethane
or aromatic urethane, and their pharmaceutically
acceptable salts.

2. Pharmacologically active peptides of the following
formulas:

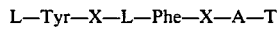

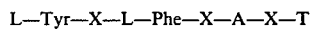

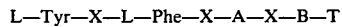

wherein:
  X is any amino acid of the group consisting of D-alanine, D-threonine, D-serine, D-methionine, D-valine, D-phenylalanine, D-leucine, D-isoleucine, D-arginine, D-histamine, D-proline, D-hydroxyproline, D-lysine, D-glutamine, D-glutamic acid, D-asparagine, D-aspartic acid;
  L—Phe is the amino acid residue of L-phenylalanine;
  A represents an aromatic amino acid selected from the group consisting of tyrosine and phenylalanine;
  B represents tyrosine, phenylalanine or glycine;
  T represents OH, OR, NH$_2$, NHR, NR$_2$ or NH—NHR' in which R is a substituted linear or branched 1-10C-alkyl, adamantyl, 1-10C-cycloalkyl or 6-8C-aralkyl, phenyl, benzyl or phenylethyl and R' represents hydrogen, linear or branched 1-10C alkyl, cycloalkyl or 6-8C-aralkyl, 2-8C-alkenyl, linear, branched or cyclic aliphatic 1-16C-acyl, which can be substituted by OH, NH$_2$, 1-4C-alkoxy or halogen, aromatic acyl which can be substituted by OH, NH$_2$, halogen, or 1-4C-alkoxy; linear, branched or cyclic 3-11C-aliphatic urethane or aromatic urethane, and their pharmaceutically acceptable salts;
  L—Tyr is the N-terminal amino acid residue of the general formula:
  (a)

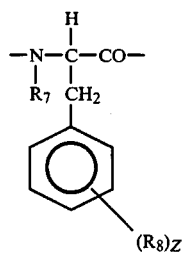

wherein:
  R$_3$ represents hydrogen or an alkyl group with 1-4 C-atoms;
  R$_4$ represents hydrogen or together with R$_3$ represents an ethylene bond;
  R$_5$ represents hydrogen, an alkyl group with 1-4 C-atoms or a R$_6$CO-group;
  R$_6$ represents a saturated or unsaturated linear or branched alkyl residue with 1-17 C-atoms, a phenyl residue or a phenyl-alkyl residue with 7-12 C-atoms, wherein the phenyl residues can be substituted by 1 or 2 substituents from the halogen series, alkyl with 1-4 C-atoms or alkoxy with 1 to 4 C- atoms, wherein the R$_5$O-group is in the meta position or para position to

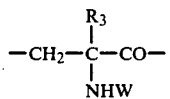

W represents hydrogen, alkyl with 1 to 5 C-atoms, alkenyl with 3-5 C-atoms, cyclopropylmethyl, cyclobutylmethyl, and R$_6$CO—
(b) the phenylalanine of the general formula:

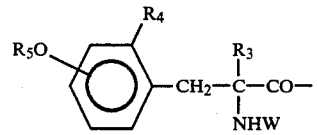

wherein:
  R$_7$ represents hydrogen or alkyl with 1-4 C-atoms;
  R$_8$ represents hydrogen, fluorine, chlorine, bromine, nitro, alkyl with 1-4 C-atoms or alkoxy with 1-4 C-atoms; and
  Z is 1 or 2.

3. Pharmacologically active peptides of the following formulas:

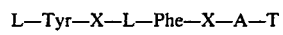

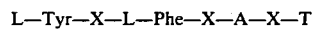

wherein:
  L—Tyr is the N-terminal amino acid residue L-tyrosine;
  X is any amino acid of the group consisting of D-dehydroalanine, D-threonine, D-serine, D-methionine, D-valine, D-dehydrophenylalanine, D-leucine, D-isoleucine, D-arginine, D-histamine, D-proline, D-hydroxyproline, D-lysine, D-glutamine, D-glutamic acid, D-asparagine, D-aspartic acid;
  L—Phe is the amino acid residue of L-dehydrophenyl-alanine;
  A represents an aromatic amino acid selected from the group consisting of dehydrotyrosine and dehydrophenylalanine;
  B represents dehydrotyrosine, dehydrophenylalanine, or dehydroglycine;
  T represents OH, OR, NH$_2$, NHR, NR$_2$ or NH—NHR' in which R is a substituted linear or branched 1-10C-alkyl, adamantyl, 1-10C-cycloalkyl or 6-8C-aralkyl, phenyl, benzyl or phenylethyl and R' represents hydrogen, linear or branched 1-10C alkyl, cycloalkyl or 6-8C-aralkyl, 2-8C-alkenyl, linear, branched or cyclic aliphatic 1-16C-acyl, which can be substituted by OH, NH$_2$, 1-4C-alkoxy or halogen, aromatic acyl which can be substituted by OH, NH$_2$, halogen, or 1-4C-alkoxy; linear, branched or cyclic 3-11C-aliphatic urethane or aromatic urethane, and their pharmaceutically acceptable salts.

4. Pharmacologically active peptides of the following formulas:

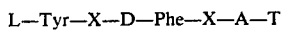
L—Tyr—X—D—Phe—X—A—T

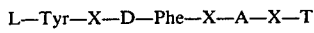
L—Tyr—X—D—Phe—X—A—X—T

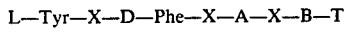
L—Tyr—X—D—Phe—X—A—X—B—T wherein:
L—Tyr is the N-terminal amino acid residue L-tyrosine;
X is any amino acid of the group consisting of D-alanine, D-dehydroalanine, D-threonine, D-serine, D-methionine, D-valine, D-phenylalanine, D-dehydrophenylalanine, D-leucine, D-isoleucine, D-arginine, D-histamine, D-proline, D-hydroxyproline, D-lysine, D-glutamine, D-glutamic acid, D-asparagine, D-aspartic acid;
D—Phe is the amino acid residue of D-phenylalanine and D-dehydrophenylalanine;
A represents an automatic amino acid selected from the group consisting of tyrosine, dehydrotyrosine, phenylalanine, and dehydrophenylalanine;
B represents tyrosine, phenylalanine, glycine, dehydrotyrosine, dehydrophenylalanine, and dehydroglycine;
T represents OH, OR, $NH_2$, NHR, $NR_2$ or NH—NHR' in which R is a substituted linear or branched 1-10C-alkyl, adamantyl, 1-10C-cycloalkyl or 6-8C-aralkyl, phenyl, benzyl or phenylethyl and R' represents hydrogen, linear or branched 1-10C alkyl, cycloalkyl or 6-8C-aralkyl, 2-8C-alkenyl, linear, branched or cyclic aliphatic 1-16C-acyl, which can be substituted by OH, $NH_2$ 1-4C-alkoxy or halogen, aromatic acyl which can be substituted by OH, $NH_2$, halogen, or 1-4C-alkoxy; linear, branched or cyclic 3-11C-aliphatic urethane or aromatic urethane, and their pharmaceutically acceptable salts;
L-Tyr is an N-terminal amino acid residue of L-tyrosine and amino acid residues of the general formula (a)

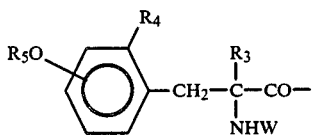

wherein:
$R_3$ represents hydrogen or an alkyl group with 1-4 C-atoms;
$R_4$ represents hydrogen or together with $R_3$ represents an ethylene bond;
$R_5$ represents hydrogen, an alkyl group with 1-4 C-atoms or a $R_6$CO-group;
$R_6$ represents a saturated or unsaturated linear or branched alkyl residue with 1-17 C-atoms, a phenyl residue or a phenyl-alkyl residue with 7-12 C-atoms, wherein the phenyl residues can be substituted by 1 or 2 substituents from the halogen series, alkyl with 1-4 C-atoms or alkoxy with 1 to 4 C-atoms, wherein the $R_5$O-group is in the meta position or para position to

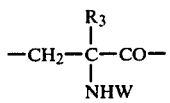

W represents hydrogen, alkyl with 1 to 5 C-atoms, alkenyl with 3-5 C-atoms, cyclopropylmethyl, cyclobutylmethyl, and $R_6$CO—

(b) the phenylalanine of the general formula:

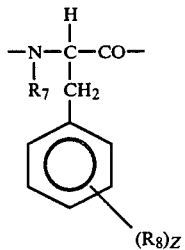

wherein:
$R_7$ represents hydrogen or alkyl with 1-4 C-atoms;
$R_8$ represents hydrogen, fluorine, chlorine, bromine, nitro, alkyl with 1-4 C-atoms or alkoxy with 1-4 C-atoms; and
Z is 1 or 2.

5. Pharmacologically active peptides according to claim 1 characterized in that the peptides have the following formulas:

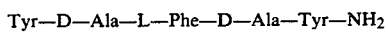
Tyr—D—Ala—L—Phe—D—Ala—Tyr—$NH_2$

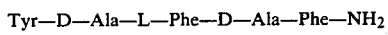
Tyr—D—Ala—L—Phe—D—Ala—Phe—$NH_2$

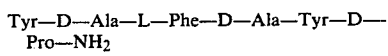
Tyr—D—Ala—L—Phe—D—Ala—Tyr—D—Pro—$NH_2$

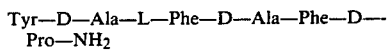
Tyr—D—Ala—L—Phe—D—Ala—Phe—D—Pro—$NH_2$

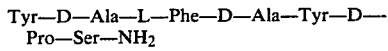
Tyr—D—Ala—L—Phe—D—Ala—Tyr—D—Pro—Ser—$NH_2$

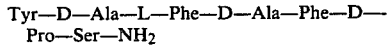
Tyr—D—Ala—L—Phe—D—Ala—Phe—D—Pro—Ser—$NH_2$

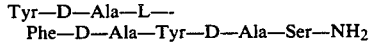
Tyr—D—Ala—L—Phe—D—Ala—Tyr—D—Ala—Ser—$NH_2$

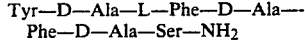
Tyr—D—Ala—L—Phe—D—Ala—Phe—D—Ala—Ser—$NH_2$

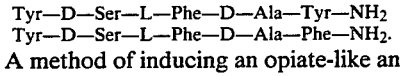
Tyr—D—Ser—L—Phe—D—Ala—Tyr—$NH_2$
Tyr—D—Ser—L—Phe—D—Ala—Phe—$NH_2$.

6. A method of inducing an opiate-like analgtic activity and blood pressure lowering in a patient comprising administering to a patient a safe and effective amount in the range of 0.001 to 100 mg per kilogram body weight of a peptide defined in any one of claims 1 to 5.

* * * * *